(12) United States Patent
Stockemann et al.

(10) Patent No.: US 6,225,297 B1
(45) Date of Patent: May 1, 2001

(54) COMBINATION CONTRACEPTIVE

(75) Inventors: Klaus Stockemann; Kristof Chwalisz, both of Berlin (DE)

(73) Assignee: Schering Akitiengesellschaft, Berlin (DE)

( * ) Notice: Subject to any disclaimer, the term of this patent is extended or adjusted under 35 U.S.C. 154(b) by 0 days.

(21) Appl. No.: 08/666,592

(22) PCT Filed: Dec. 22, 1994

(86) PCT No.: PCT/EP94/04273

§ 371 Date: Nov. 1, 1996

§ 102(e) Date: Nov. 1, 1996

(87) PCT Pub. No.: WO95/17193

PCT Pub. Date: Jun. 29, 1995

(30) Foreign Application Priority Data

Dec. 22, 1993 (DE) .................................. 43 44 463

(51) Int. Cl.$^7$ .......................... A61K 31/57; A61K 31/565
(52) U.S. Cl. .................... 514/170; 514/171; 514/178; 514/179; 514/180; 514/843
(58) Field of Search .................... 514/170, 171, 514/179, 178, 180, 843

(56) References Cited

U.S. PATENT DOCUMENTS

| | | | | |
|---|---|---|---|---|
| 3,890,356 | * | 6/1975 | Grunwell et al. | 260/397.5 |
| 3,928,398 | * | 12/1975 | Grunwell et al. | 260/397.5 |
| 4,000,273 | * | 12/1976 | Grunwell et al. | 424/238 |
| 4,018,919 | * | 4/1977 | Black | 424/242 |
| 4,670,426 | * | 6/1987 | Zor et al. | 514/171 |
| 5,439,913 | * | 8/1995 | Chwalisz et al. | 514/277 |
| 5,516,769 | * | 5/1996 | Hodgen | 514/179 |
| 5,622,943 | * | 4/1997 | Hodgen | 514/179 |

FOREIGN PATENT DOCUMENTS 0 639 970 * 1/1998 (EP) .
93/23020 * 11/1993 (WO) .
WO 93/21927 * 11/1993 (WO) .
94/18982 * 9/1994 (WO) .

OTHER PUBLICATIONS

Kekkonen et al., Fertil Steril, 60(4), pp. 610–615, 1993.*
Kekkonen et al., Fertil Steril, 53(4), pp. 747–750, 1990.*
Chemical Abstracts, vol. 109, abstract 122618x, 1990.*
Drug Facts and Comparisons, Oral Contraceptives, Progestin–Only Products, 1989.*
Marcelo C. Batista, MD, et al.; "Delayed endometrial maturation induced by daily administration of the antiprogestin RU 486: A potential new contraceptive strategy"; Jul. 1992; vol. 167; No. 1; pp. 60–65.*
Kenneth A. Steingold, MD; "Antiprogestins in Reproductive Medicine"; Jan. 1992; Sex Steroids vol. 3; No. 1; pp. 233–249.*
P.C. Ishwad; "Treatment with a Progesterone Antagonist ZK 98.299 Delays Endometrial Development without Blocking Ovulation in Bonnet Monkeys"; Jul. 1993, Contraception 48, pp. 57–70.*
Gary D. Hodgen, PhD; "Progesterone antagonists: Useful for contraception?"; 1988; Contemporary OB/GYN Special Issue, pp. 65–66.*
L. Michael Kettel, MD; "Endocrine responses to long–term administration of the antiprogesterone RU486 in patients with pelvic endometriosis"; Fertility and Strility vol. 56; No. 3; Sep. 1991; pp. 402–407.*

* cited by examiner

*Primary Examiner*—Richard L. Raymond
(74) *Attorney, Agent, or Firm*—Millen, White, Zelano & Branigan

(57) ABSTRACT

This invention relates to a combination product that consists of individual dosage units of a competitive progesterone antagonist and, in addition, sequentially provided individual dosage units of a compound with gestagenic action, as well as its use for the production of contraceptives based on the inhibition of implantation (receptivity inhibition).

23 Claims, No Drawings

COMBINATION CONTRACEPTIVE

This application is a 371 of PCT/EP94/04273, filed Dec. 22, 1994.

This invention relates to a combination product that consists of individual dosage units of a competitive progesterone antagonist and, in addition, sequentially provided individual dosage units of a compound with gestagenic action, as well as its use for the production of contraceptives based on the inhibition of implantation (receptivity inhibition).

It is known that competitive progesterone antagonists (antigestagens=AG's), such as, e.g., RU 486 (mifepristones; 11β-[(4-N,N-dimethylamino)-phenyl]-17β-hydroxy-17α-propinyl-4,9(10)-estradien-3-one) are able to inhibit ovulation in various animal species and in women [1) Uilenbroek J. TH. J (1991): Hormone Concentrations and Ovulatory Response in Rats Treated with Antiprogestagens. Journal of Endocrinology, 129, 423–429; 2) Danforth, R. et al. (1989): Contraceptive Potential of RU 486 by Ovulation Inhibition: III. Preliminary Observations on Once Weekly Administration, Contraception, 40/2, 195–200; 3) Kekkonen R. et al. (1990): Interference with Ovulation by Sequential Treatment with the Antiprogestin RU 486 and Synthetic Progestin. Fertility and Sterility, 53/4, 747–750; 4) Ledger W. L. et al. (1992): Inhibition of Ovulation by Low Dose Mifepristone (RU 486). Human Reproduction, 7/7, 945–950; 5) Nieman L. K. et al. (1987): The Progesterone Antagonist RU 486: A New Potential New Contraceptive Agent. The New England Journal of Medicine, 316/4, 187-1991].

The implantation of a fertilized egg can also be prevented by AG's (implantation inhibition); [6) Glassier A. et al. (1992): Mifepristone (RU 486) Compared with High Dose Estrogen and Progesterone for Emergency Postcoital Contraception: New England Journal of Medicine, 8/15; 1041; 7) Puri C. P. et al. (1990): Effects of a Progesterone Antagonist, Ilopristone, On Induction of Menstruation, Inhibition of Nidation, and Termination of Pregnancy in Bonnet Monkeys. Biology of Reproduction, 43, 437–443; 8) Ishwad P. C. et al. (1993): Treatment with a Progesterone Antagonist ZK 98 299 Delays Endometrial Development without Blocking Ovulation in Bonnet Monkeys. Contraception, 48, 57–70; 9) Batista M. C. et al. (1992): Delayed Endometrial Maturation Induced by Daily Administration of the Antiprogestin RU 486: A Potential New Contraceptive Strategy. AM. J. Obstet. Gynecol. 167/1, 60–65].

It should be possible to use AG's as contraceptives because of their ovulation-inhibiting action [3), 4), 5)] or implantation-inhibiting action [6), 7), 8), 9)]. The use of competitive progesterone antagonists in a non-ovulation-inhibiting as well as a non-abortion-inducing dose for the production of oral contraceptives is described in International Patent Application WO-A 93/23020.

In addition, for gynecological applications, initial clinical studies have shown that AG's can be used for the treatment of endometriosis and leiomyomata uteri [10) Kettel L. M. et al. (1991): Endocrine Responses to Long-Term Administration of the Antiprogesterone RU 486 in Patients with Pelvic Endometriosis. Fertility and Sterility, 56/3, 402–407; 11) Kettel L. M. et al. (1993): Long-Term, Low-Dose RU 486 in the Treatment of Endometriosis. Meeting of the Society of Gynecological Investigation 1993, Abstract S-136; 12) Murphy A. A. et al. (1993): Regression of Uterine Leiomyomata in Response to the Antiprogestin RU 486, J. Clin. Endocrinol. Metab., 76/2, 513–517].

The findings of these studies indicate that in the case of chronic treatment with AG's over the entire menstrual cycle, but also in the case of treatment during specific cycle phases with AG's, the elimination of the progesterone action during the luteal phase of the cycle can lead to displacement or lengthening of the cycle with cessation of menstruation (amenorrhea) or weakened menstruation [8), 9), 10)].

Menstruation, however, means natural protection for the endometrium. In the normal menstrual cycle, in the follicle phase (proliferation phase) proliferation of the endometrium occurs under the action of estrogens. Subsequently, growth inhibition of the endometrium that is caused by progesterone takes place with conversion into a secretorily active endometrium in the luteal phase (secretion phase). At the end of this phase, menstruation of the endometrium occurs, during which portions of this tissue are shed.

If, however, during treatment with a competitive progesterone antagonist, the action of progesterone on the endometrium is completely blocked in the luteal phase, the proliferative influence of the estrogens on the endometrium predominates. In addition to stopping the conversion into a secretory endometrium and the thus deficient [10)] subsequent bleeding (induction of amenorrhea) or reduced bleeding [(8)] because of the so-called "unopposed estrogen effect," long-term stimulation of the endometrium can result [13) Murphy A. A. et al. (1993): Endometrial Effect of a Long-Term, Low-Dose Administration of RU 486 in Cycling Women. Meeting of the Society of Gynecological Investigation 1993, Abstract S-138].

This can increase the risk of an endometrium hyperplasia or the development of an endometrial carcinoma [14) Galle P. C. and McRae M. A. (1992): Amenorrhea and Chronic Anovulation. Finding and Addressing the Underlying Cause. Postrad. Med., 92/2, 255–260; 15) Johansson ED. et al. (1981): Unopposed Endogenous Estrogens and the Incidence of Cancer in Female Reproductive Organs. Acta Obstet. Gynecol. Scand. Suppl., 101, 17–20].

The object of this invention is to improve the already known use of competitive progesterone antagonists for contraception based on receptivity inhibition in such a way that the undesirable actions do not occur or occur only to a slight extent during continuous treatment with competitive progesterone antagonists, such as, e.g., persistent amenorrhea, endometrial hyperplasia, etc., so that more efficient and more reliable treatment as well as better cycle control are ensured.

This object is achieved by the product according to the invention that contains in combination in a packaging unit individual dosage units of a competitive progesterone antagonist and individual dosage units of a gestagen for its sequential, oral administration, in which each individual dosage unit that contains the competitive progesterone antagonist contains the latter in a non-ovulation-inhibiting as well as non-abortion-inducing amounts.

The endometrium is transformed by the sequential administration of a gestagen during the pause in treatment with the competitive progesterone antagonist and converted into a secretorily active endometrium and thus prepared for bleeding—induced by the subsequent administration of the antigestagen.

A contraceptive method with sequential treatment with antigestagens for ovulation inhibition, followed by gestagen, has already been described [3)]. The dose that inhibits ovulation depends to a great extent on the species in question and for, e.g., RU 486 is 2–5 mg in women [Ledger W. L. et al., 4)].

In the contraceptively active combination product that is proposed according to the invention, the competitive progesterone antagonist is to be administered in a dose that is not ovulation-inhibiting. In this case, the progesterone antagonist inhibits, i.a., the development of endometrial glands, which must function in order for the implantation of a fertilized egg in the uterus to occur (thus inhibiting the receptivity of the endometrium), but does not interfere with ovulation. As a result, impairment of the ovarian cycle is avoided. After the receptive phase of the endometrium in the normal cycle, which is inhibited by competitive progesterone antagonists, the endometrium is again prepared by the gestagen—corresponding to the normal cycle in the luteal phase—for bleeding that is induced by the progesterone antagonists that are administered after the administration of gestagen (see Diagram 1).

In the normal cycle, two phases are distinguished: the proliferation phase (follicle phase) and the secretion phase (luteal phase). In the follicle phase, estrogen-induced development of the secretory glands in the endometrium occurs in the normal menstrual cycle, while in the luteal phase the gestagen (progesterone) induces the secretory activity of the glands. According to this invention, the progesterone antagonist serves to inhibit both the development of endometrial glands as early as during the follicle phase and the secretory conversion of glands in the luteal phase, which is essential for successful implantation of the fertilized egg. Since treatment with a competitive progesterone antagonist does not result in complete suppression of estrogens, [the levels are comparable to those in the average follicle phase (10)], the endometrium (corresponding to the normal cycle) is converted by a gestagen after the inhibition of the receptive phase (only in this phase could implantation occur—if it is not inhibited) and prepared for bleeding that corresponds to natural menstruation, which is induced by continued AG treatment.

The fact that bleeding can be induced by competitive progesterone antagonists is described [5]. This is also possible in the presence of progesterone [16] Croxatto, H. B.; Spitz, I. M.; Salvatierra A. M., and Bardin C. W. (1985). The Demonstration of the Antiprogestin Effects of RU 486 When Administered to the Human During hCG-Induced Pseudopregnancy. In Baulieu E. E. and Segal S. J. (eds.). The Antiprogestin Steroid RU 486 and Human Fertility Control. Plenum Press, New York, pp. 263–269].

Sequential treatment with gestagen ensures suitable cycle control.

The undesirable effects of possible monotherapy with a competitive progesterone antagonist (chronic amenorrhea and stimulation of the endometrium) can be prevented with the proposed composition.

A pause in the treatment with the competitive progesterone antagonist of 2 to 12, preferably 5–10 days, in which a gestagen is provided in an effective dose of 2 to 12, preferably 5 to 10 days, prepares the endometrium for bleeding (transformation into a secretory tissue). The subsequent continuing treatment with a competitive progesterone antagonist (non-ovulation-inhibiting dose) simulates the natural drop in progesterone (progesterone blocking) and triggers menstruation, in which portions of the endometrium are shed. By regular daily administration of a gestagen over a specific period in an effective dose, e.g., every 28 days (length of an untreated cycle) or at, e.g., intervals that correspond to three normal, untreated cycles, the endometrium is prepared for bleeding-induction by a competitive progesterone antagonist. Thus, the manifestation of lasting amenorrhea or endometrium hyperplasia that is caused by the deficient conversion of the endometrium in the luteal phase, which can result with chronic treatment with AG alone, is prevented and thus better cycle control is ensured. The endometrium is protected against the above-described effects by regular induction of bleeding (simulation of natural bleeding).

In diagrams 1, 2 and 3, by way of example, different possible configurations of the composition are depicted.

In the product according to the invention, the gestagen that is sequentially administered to the competitive progesterone antagonist is intended for administration at the earliest starting on the 18th day after the first administration of the competitive progesterone antagonist.

The number of dosage units of the competitive progesterone antagonist to be administered as well as the number of gestagen-containing dosage units that are subsequently to be administered daily can be selected in such a way that the menstruation that is triggered by the administration of gestagen corresponds in time to menstruation in an untreated cycle (diagram 1)).

The composition according to the invention can also contain the dosage units of gestagen that are to be administered sequentially to the competitive progesterone antagonist, arranged in such a way that they are provided at the latest after 3×28-day (corresponding to the period of three normal, untreated cycles) administration of the progesterone antagonist (Diagram 3)).

Between these two limits (competitive progesterone antagonist over a period of 18 or 3×28 days), all conceivable cases are possible, thus, e.g., 2×28 days-administration of the competitive progesterone antagonist, then gestagen administration.

As competitive progesterone antagonists according to this invention, all compounds are considered that themselves or their metabolic products block the action of the progesterone on its receptor. As examples of typical representatives, the following can be mentioned here:

11β-((4-N,N-Dimethylamino)-phenyl)-17β-hydroxy-17α-propinyl-4,9(10)-estradien-3-one (RU-486), 11β-((4-N,N-dimethylamino)-phenyl)-17β-hydroxy-18-methyl-17α-propinyl-4,9(10)-estradien-3-one, 11β-((4-N,N-dimethylamino)-phenyl)-17αβ-hydroxy-17aα-propinyl-D-homo-4,9(10),16-estratien-3-one, 11β-p-methoxyphenyl-17β-hydroxy-17α-ethinyl-4,9(10)-estradien-3-one (Steroids 37 (1981), 361–382), 11β-(4-acetylphenyl)-17β-hydroxy-17α-(prop-1-inyl)-4,9(10)-estradien-3-one (EP-A 0 190 759), the 19,11β-bridged steroids from EP-A-0 283 428, the 10β-H steroids from EP-A-0 404 283, 11β-[(4-dimethylamino)phenyl]-17α-hydroxy-17β-(3-hydroxypropyl)-13α-methyl-4,9(10)-gonadien-3-one (onapristone; EP-A-0 129 499);

11β,19-(4-acetylphenyl)-17β-hydroxy-17α-(3-hydroxyprop-1(Z)-enyl)-4,9(10)-estradien-3-one (EP-A-0 190 759);

11β,19-(4-(cyanophenyl)-17β-hydroxy-17α-(3-hydroxyprop-1(Z)-enyl)-4-androsten-3-one, 11β,19-(4-(3-pyridinyl)-o-phenylene)-17β-hydroxy-17a-(3-hydroxyprop-1(Z)-enyl)-4-androsten-3-one (both WO-A 93/23020).

This list is not exhaustive; other competitive progesterone antagonists described in the above-mentioned publications as well as those from publications that are not mentioned here are also suitable.

For this invention, especially those competitive progesterone antagonists are suitable that are peripherally selectively active, i.e., in which the endometrial action is pronounced, while at the dose in question, no action or only a slight central action via the hypophyseal-ovarian axis is observed (see WO-A 93/23020).

For the purposes of this invention, the competitive progesterone antagonists can be administered locally, topically, enterally, transdermally, or parenterally.

For the preferred oral administration, especially tablets, coated tablets, capsules, pills, suspensions, or solutions are suitable, which can be produced in the usual way with the additives and vehicles that are commonly used in galenicals.

The formulation of the competitive progesterone antagonist is done analogously to what is known, for example, for RU 486.

For local or topical application, for example, vaginal suppositories, vaginal gels, implants, vaginal rings, or transdermal systems such as skin patches are suitable.

A dosage unit contains about 0.1 to 50 mg of 11β-[(4-dimethylamino)phenyl]-17α-hydroxy-17β-(3-hydroxypropyl)-13α-methyl-4,9(10)-gonadien-3-one (onapristone=peripherally selective, dissociated competitive progesterone antagonist), 0.1–5.0 mg of 11β-((4-N,N-dimethylamino)-phenyl)-17β-hydroxy-17α-propinyl-4,9 (10)-estradien-3-one (RU 486=nondissociated competitive progesterone antagonist) or a biologically equivalent amount of another competitive progesterone antagonist.

If the administration of the competitive progesterone antagonist to be used according to the invention is carried out by an implant, a vaginal ring or a transdermal system, these administration systems must be designed in such a way that the dose of the competitive progesterone antagonist released daily by them lies in this range of 0.25 to 50 mg of 11β-[(4-dimethylamino)phenyl]-17α-hydroxy-17β-(3-hydroxypropyl)-13α-methyl-4,9(10)-gonadien-3-one or an equivalent-action dose of another progesterone antagonist.

The dose of a competitive progesterone antagonist that is to be administered according to the invention lies in a non-ovulation-inhibiting as well as non-abortion-inducing dose range of the progesterone antagonist in question.

When peripherally selective competitive progesterone antagonists are used, 0.1–50 mg per one-time administration can be dosed since the peripherally selective substances allow a far larger dosage without resulting in ovulation inhibition.

One-time administration is also to mean that when using an administration system that continuously releases competitive progesterone antagonists, 0.25–20 mg of 0.1 to 50 mg each per day is released.

The product according to the invention is preferably designed such that the administration of the individual dosage units of the competitive progesterone antagonist can be done every 4 to every 10 days, specifically beginning on any day before the ovulation time during the first administration cycle. As a result, contraceptive reliability is already ensured in the first administration cycle (Bygdeman).

The time intervals between the administrations of individual dosage units are preferably to be constant in this case.

The product according to the invention especially provides for administration of the respective dosage units of the competitive progesterone antagonist in such a way that the latter are administered once per week respectively on the same day of the week, for example, on a Monday ("Monday pill").

High intake reliability is ensured by the weekly administration cycle on the same day every week.

The product according to the invention can also provide for the administration of the individual dosage units of the competitive progesterone antagonist daily, every second or every third day.

Equivalent-action dose amounts of various competitive progesterone antagonists are determined in the test of anti-gestagenic action on rabbits (elimination of endometrium transformation).

As gestagens, according to this invention, all compounds are suitable that are suitable for use in oral contraceptives because of their gestagenic activity. A list of such compounds is found in B. Runnebaum et al., "Female Contraception: Update and Trends," Springer-Verlag, Berlin, 1988, pages 64–90, 109–121, 122–128 and 129–140.

Preferred gestagens within the scope of this invention are gestodene, progesterone, levonorgestrel, cyproterone acetate, chlormadinone acetate, drospirenone (dihydrospirorenone), norethisterone, norethisterone acetate, norgestimate, desogestrel or 3-ketodesogestrel.

In the product according to this invention, the gestagen is present in a dosage form that is suitable for oral administration, namely as a tablet, coated tablet, capsule or pill.

In this case, the formulation of the gestagen is done in a way analogous to preparing gestagens for hormonal contraception with use of the adjuvants that are commonly used for this purpose.

A daily dosage unit of the gestagen contains the latter at a dose of 0.6–6.0 mg of levonorgestrel, 2–20 mg of cyproterone acetate, 0.3–3.0 mg of gestodene or 0.2–2.0 mg of desogestrel or an amount of another gestagen that is equivalent in action to these dosages.

Determining equivalent-action dose amounts of various gestagens is done according to known methods; further details are found in, for example, the two articles "Probleme der Dosisfindung: Sexualhormone [Problems of Dose-Finding: Sex Hormones]"; F. Neumann et al. in "Arzneimittelforschung [Drug Research]" 27, 2a, 296–318 (1977) as well as "Aktuelle Entwicklungen in der hormonalen Kontrazeption [Current Developments in Hormonal Contraception]"; H. Kuhl in "Gynäkologe [Gynecologists]" 25: 231–240 (1992).

EXAMPLES

Once per 28-day cycle of several days of gestagen:
1)
/-----------1st cycle----------/--------------2nd cycle-----------/
-----------3rd cycle--------/etc.
Day:                 Day:              Day:
1---AG---21/22---P---28/1---AG---21/22---P---28/1---AG---21/22---P---28

----→ Bleeding    ----→ Bleeding
2)
Day:                 Day:              Day:
1---AG---23/24---P---28/1---AG---23/24---P---28/1---AG---23/24---P---28

---→ Bleeding   ---→ Bleeding

Once after three cycles (1 cycle = 28 days) gestagen for several days:
3)
/-----1st cycle----/-----2nd cycle----/----3rd cycle----/
1----AG----28/1----AG----28/1----AG----28/1----P----10/11---
--AG---28 etc.
                                                      ----→
Bleeding AG stands for "competitive progesterone antagonist" and P stands for "gestagen"

What is claimed is:

1. A product that contains in combination individual dosage units of a competitive progesterone antagonist and individual dosage units of a gestagen useful for its sequential, oral administration, in which the amount of the competitive progesterone antagonist in each of its individual dosage units is non-ovulation-inhibiting and non-abortion-inducing.

2. The product according to claim 1, in which the amount of the competitive progesterone antagonist in each of its individual dosage units is effective for once-daily to once-weekly administration.

3. The product according to claim 2, in which the amount of the competitive progesterone antagonist in each of its individual dosage units is effective for once-daily administration.

4. The product according to claim 2, in which the amount of the competitive progesterone antagonist in each of its individual dosage units is effective for once-weekly administration.

5. The product according to claim 1, in which the amount of the gestagen in each of its individual dosage units is effective for daily administration on successive days.

6. The product according to claim 1, in which the gestagen is distributed in 2 to 12 dosage units.

7. The product according to claim 6, in which the dosage units are arrayed according to a sequential schedule for their administration, so that the gestagen units are to be administered sequentially starting on day 18 or later after the first dosage unit of the competitive progesterone antagonist is to be administered.

8. The product according to claim 7, in which the dosage units are arrayed so that the gestagen units are to be administered starting on day 21 or 22 after the first dosage unit of the competitive progesterone antagonist is to be administered.

9. The product according to claim 1, in which the competitive progesterone antagonist dosage units contain at least one compound selected from the group consisting of 11$\beta$-((4-N,N-dimethylamino)-phenyl)-17$\beta$-hydroxy-17$\alpha$-propinyl-4,9(10)-estradien-3-one, 11$\beta$-((4-N,N-dimethylamino)-phenyl)-17$\beta$-hydroxy-18-methyl-17$\alpha$-propinyl-4,9(10)-estradien-3-one, 11$\beta$-((4-N,N-dimethylamino)-phenyl)-17$\alpha\beta$-hydroxy-17a$\alpha$-propinyl-D-homo-4,9(10), 16-estratien-3-one, 11$\beta$-p-methoxyphenyl-17$\beta$-hydroxy-17$\alpha$-ethinyl-4,9(10)-estradien-3-one, 11$\beta$-(4-acetylphenyl)-17$\beta$-hydroxy-17$\alpha$-(prop-1-inyl)-4,9(10)-estradien-3-one, 11$\beta$-((4-dimethylamino)phenyl)-17$\alpha$-hydroxy-17$\beta$-(3-hydroxypropyl)-13$\alpha$-methyl-4,9(10)-gonadien-3-one, 11$\beta$,19-(4-acetylphenyl)-17$\beta$-hydroxy-17$\alpha$-(3-hydroxyprop-1(Z)-enyl)-4,9 (10)-estradien-3-one, 11$\beta$,19-(4-(cyanophenyl)-17$\beta$-hydroxy-17$\alpha$-(3-hydroxyprop-1(Z)-enyl)-4-androsten-3-one, and 11$\beta$,19-(4-(3-pyridinyl)-o-phenylene)-17$\beta$-hydroxy-17a-(3-hydroxyprop-1(Z)-enyl)-4-androsten-3-one.

10. The product according to claim 1, in which the amount of the competitive progesterone antagonist in each individual dosage unit is 0.1 to 50 mg of 11$\beta$-((4-dimethylamino)phenyl)-17$\alpha$-hydroxy-17$\beta$-(3-hydroxypropyl)-13$\alpha$-methyl-4,9(10)-gonadien-3-one, 0.1–5.0 mg of 11$\beta$-((4-N,N-dimethylamino)-phenyl)-17$\beta$-hydroxy-17$\alpha$-propinyl- 4,9(10)-estradien-3-one or a biologically equivalent amount of another competitive progesterone antagonist.

11. The product according to claim 1, in which the gestagen dosage units contain at least one of gestodene, progesterone, levonorgestrel, cyproterone acetate, chlormadinone acetate, drospirenone, norethisterone, norethisterone acetate, norgestimate, desogestrel, 3-ketodesogestrel or another artificial or natural gestagen.

12. The product according to claim 1, in which the amount of the gestagen in each individual dosage unit is 0.6–6.0 mg of levonorgestrel, 2–20 mg of cyproterone acetate, 0.3–3.0 mg of gestodene or 0.2–2.0 mg of desogestrel or an equivalent of another gestagen.

13. A method of contraception, comprising administering to a patient an effective amount of a competitive progesterone antagonist and an effective amount of a gestagen, wherein the amount of said competitive progesterone antagonist does not inhibit ovulation or induce abortion.

14. The method of claim 13, wherein said effective amounts of competitive progesterone antagonist and gestagen are administered sequentially.

15. The method of claim 13, wherein said effective amounts of competitive progesterone antagonist and gestagen are administered simultaneously.

16. The method of claim 13, wherein said competitive progesterone antagonist and said gestagen are administered orally.

17. The method of claim 13, wherein said competitive progesterone antagonist is administered daily or weekly.

18. The method of claim 13, wherein said gestagen is administered daily.

19. The method of claim 13, wherein said competitive progesterone antagonist is

11$\beta$-((4-N,N-dimethylamino)-phenyl)-17$\beta$-hydroxy-17$\alpha$-propinyl-4,9(10)-estradien-3-one, 11$\beta$-((4-N,N-dimethylamino)-phenyl)-17$\beta$-hydroxy-18-methyl-17$\alpha$-propinyl-4,9(10)-estradien-3-one, 11$\beta$-((4-N,N-dimethylamino)-phenyl)-17$\alpha\beta$-hydroxy-17a$\alpha$-propinyl-D-homo-4,9(10), 16-estratien-3-one, 11$\beta$-p-methoxyphenyl-17$\beta$-hydroxy-17$\alpha$-ethinyl-4,9(10)-estradien-3-one, 11$\beta$-(4-acetylphenyl)-17$\beta$-hydroxy-17$\alpha$-(prop-1-inyl)-4,9(10)-estradien-3-one, 11$\beta$-((4-dimethylamino)phenyl)-17$\alpha$-hydroxy-17$\beta$-(3-hydroxypropyl)-13$\alpha$-methyl-4,9(10)-gonadien-3-one, 11$\beta$,19-(4-acetylphenyl)-17$\beta$-hydroxy-17$\alpha$-(3-hydroxyprop-1(Z)-enyl)-4,9(10)-estradien-3-one, 11$\beta$,19-(4-(cyanophenyl)-17$\beta$-hydroxy-17$\alpha$-(3-hydroxyprop-1(Z)-enyl)-4-androsten-3-one, or 11$\beta$,19-(4-(3-pyridinyl)-o-phenylene)-17$\beta$-hydroxy-17a-(3-hydroxyprop-1(Z)-enyl)-4-androsten-3-one.

20. The method of claim 13, wherein the effective amount of said competitive progesterone antagonist is 0.1 to 50 mg of 11$\beta$-[(4-dimethylamino)phenyl]-17$\alpha$-hydroxy-17$\beta$-(3-hydroxypropyl)-13$\alpha$-methyl-4,9(10)-gonadien-3-one, 0.1–5.0 mg of 11$\beta$-((4-N,N-dimethylamino)-phenyl)-17$\beta$-hydroxy-17$\alpha$-propinyl-4,9(10)-estradien-3-one or a biologically equivalent amount of another competitive progesterone antagonist.

21. The method of claim 13, wherein said gestagen is gestodene, progesterone, levonorgestrel, cyproterone acetate, chlormadinone acetate, drospirenone, norethisterone, norethisterone acetate, norgestimate, desogestrel, 3-ketodesogestrel or another artificial or natural gestagen.

22. The method of claim 13, wherein the effective amount of said gestagen is 0.6–6.0 mg of levonorgestrel, 2–20 mg of cyproterone acetate, 0.3–3.0 mg of gestodene or 0.2–2.0 mg of desogestrel or an equivalent amount of another gestagen.

23. The method of claim 13, wherein said competitive progesterone antagonist and said gestagen are administered locally, topically, enterally, transdermally or parenterally.

* * * * *

UNITED STATES PATENT AND TRADEMARK OFFICE
CERTIFICATE OF CORRECTION

PATENT NO. : 6,225,297 B1  Page 1 of 1
APPLICATION NO. : 08/666592
DATED : May 1, 2001
INVENTOR(S) : Klaus Stockemann et al.

It is certified that error appears in the above-identified patent and that said Letters Patent is hereby corrected as shown below:

On the Title page, Item [73] Assignee: reads "Akitiengesellschaft" should read -- Aktiengesellschaft --
Column 7, line 39 claim 9, reads "17a-propinyl-D-homo-4,9(10), 16-estratien-3-one," should read -- 17-propinyl-D-homo-4,9(10)-16-estradien-3-one, --
Column 7, line 51 claim 9, "17a" should read -- 17 --
Column 7, line 53 claim 9, reads "which the amount" should read -- which the non-ovulation inhibiting amount --
Column 8, line 5 claim 12, reads "of another gestagen." should read -- amount of another gestagen. --
Column 8, line 32 claim 19, reads "17a-propinyl-D-homo-4,9(10), 16-estratien-3-one," should read -- 17-propinyl-D-homo-4,9(10)-16-estradien-3-one, --
Column 8, line 43 claim 19, reads "17a" should read -- 17 --
Column 8, line 45 claim 20, reads "the effective amount" should read -- which the non-ovulation inhibiting amount --

Signed and Sealed this

First Day of April, 2008

JON W. DUDAS
*Director of the United States Patent and Trademark Office*